United States Patent [19]

Lundquist

[11] 4,227,525
[45] Oct. 14, 1980

[54] INTRAVENOUS ADMINISTRATION SET

[75] Inventor: Ingemar H. Lundquist, Oakland, Calif.

[73] Assignee: Valleylab, Boulder, Colo.

[21] Appl. No.: 891,595

[22] Filed: Mar. 30, 1978

[51] Int. Cl.³ .......................................... A61M 5/00
[52] U.S. Cl. ............................................ 128/214 R
[58] Field of Search ........... 128/214 R, 214 C, 214.2; 55/355, 364, 369, 463, 159, 321, 482; 137/138, 143, 144, 177, 197; 222/188, 189

[56] References Cited

U.S. PATENT DOCUMENTS

| | | | |
|---|---|---|---|
| 3,854,907 | 12/1974 | Rising | 55/159 |
| 4,031,891 | 6/1977 | Jess | 128/214 R |
| 4,056,100 | 11/1977 | Noiles | 128/214 C |
| 4,084,606 | 4/1978 | Mittleman | 128/214 R |
| 4,113,627 | 9/1978 | Leason | 128/214 R |
| 4,116,646 | 9/1978 | Edwards | 128/214 R |
| 4,126,558 | 11/1978 | Luceyk | 128/214 R |

*Primary Examiner*—C. Fred Rosenbaum
*Attorney, Agent, or Firm*—Flehr, Hohbach, Test, Albritton & Herbert

[57] ABSTRACT

Intravenous administration set for use with a source of liquid to be administered intravenously and having a length of flexible tube with a fitting carried on one end of the same adapted to be connected to the source of liquid. A burette is provided which has a chamber formed therein. The other end of the flexible tube is mounted in the burette so that liquid passing through the tube flows into the burette chamber. A filter assembly is carried by the burette and has a recess formed therein. A projection extends into the recess and defines at least a portion of an outlet opening for withdrawing liquid from the burette chamber. The filter assembly includes a hydrophillic filter which provides the only path for the flow of liquid and gas into the recess. The member and the projection are formed in such a manner that all liquid passing through the outlet opening must pass into the recess through the filter and carry with it any gas in the recess. Tubing is connected to the outlet opening in communication with the burette chamber and is adapted to be coupled to the patient which is to be intravenously fed.

20 Claims, 7 Drawing Figures

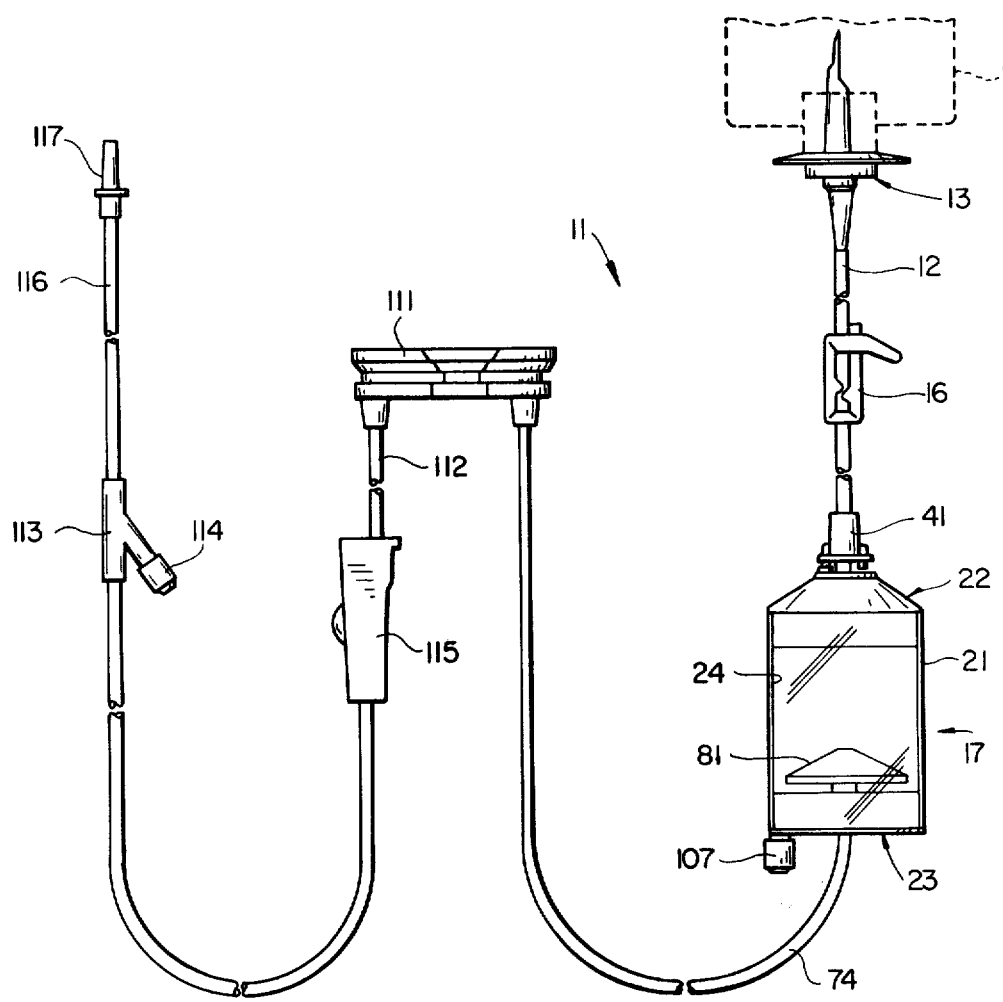
FIG_1
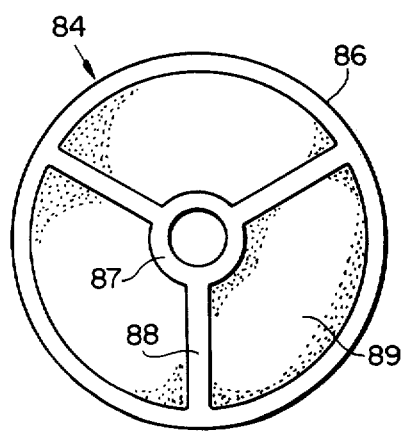
FIG_3
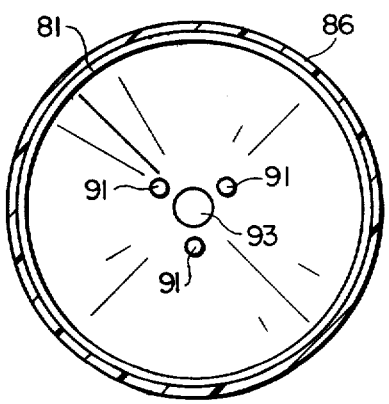
FIG_4

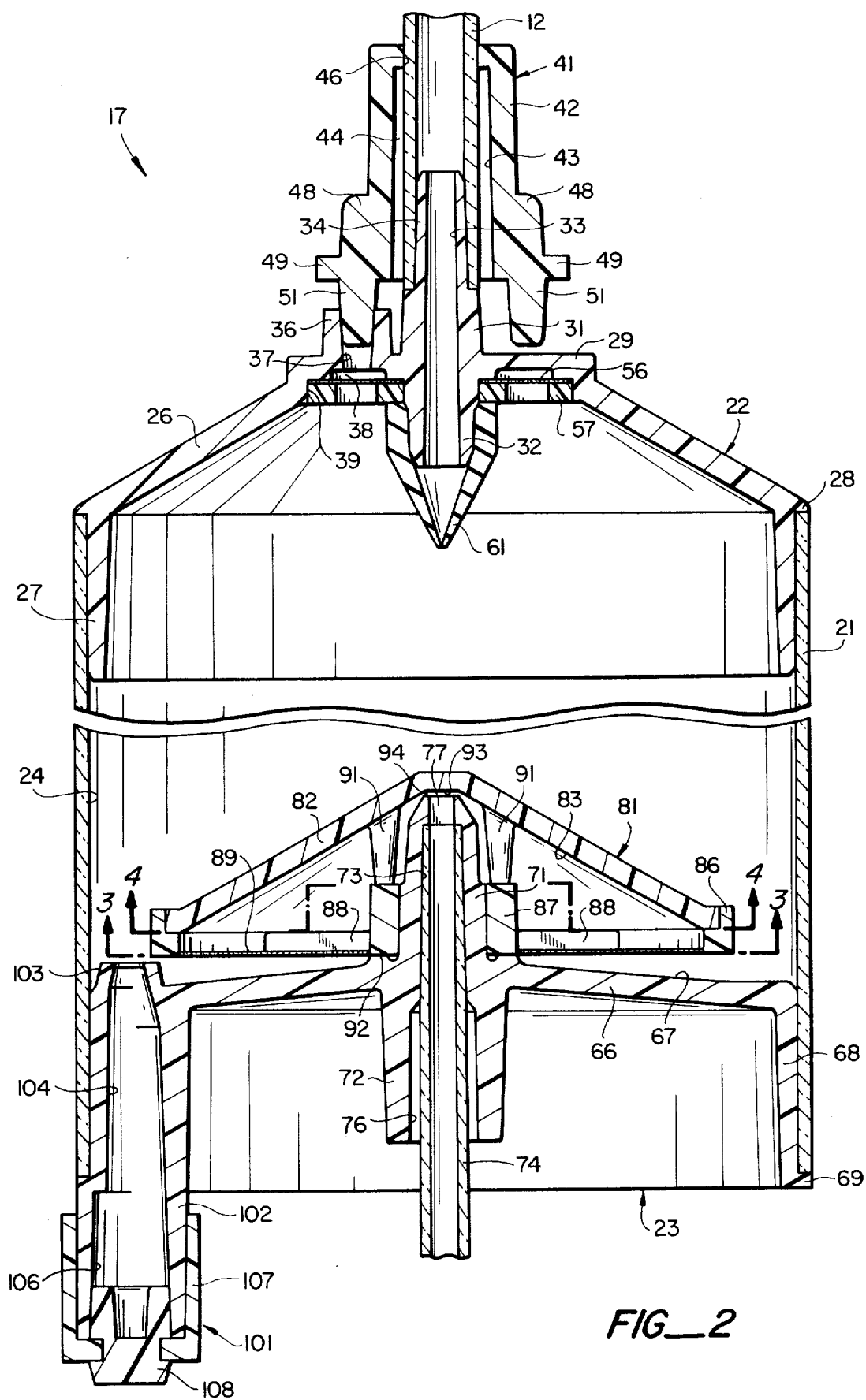
FIG_2

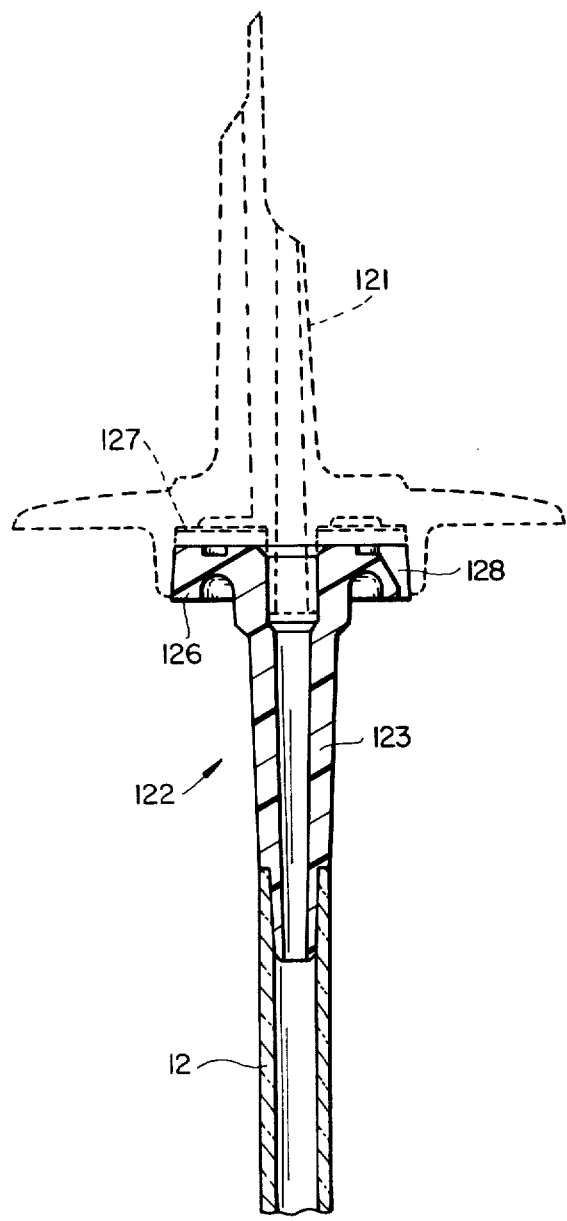
FIG_5
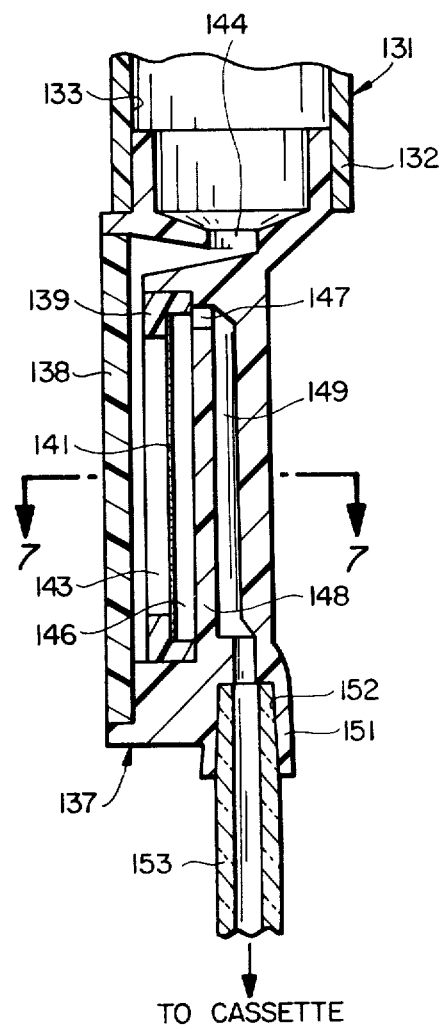
FIG_6
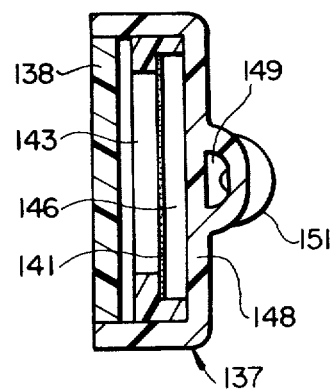
FIG_7

INTRAVENOUS ADMINISTRATION SET

BACKGROUND OF THE INVENTION

Intravenous administration sets have heretofore been provided. At least certain of these administration sets have had the drawback in that it is possible for air to be introduced into the same accidentally during use of the same. In addition to the dangers of introducing air into the administration set which could possibly be introduced into the patient with undesirable results, there is also the additional disadvantage in that the presence of air in the administration set may affect the accuracy of the pumping operation. The presence of air may also adversely affect alarm systems utilized in connection with such administration sets to give an alarm when the source of the intravenous liquid being administered is depleted. There is therefore a need for a new and improved intravenous administration set which overcomes the above named disadvantages.

SUMMARY OF THE INVENTION AND OBJECTS

The intravenous administration set is for use with a source of liquid to be administered intravenously and consists of a length of flexible tube. Means is carried by one end of the flexible tube which is adapted to be connected to the source of liquid to be administered. A burette in generally cylindrical form is provided and has a cylindrical wall forming an open-ended cylinder and top and bottom cylinder assemblies disposed in the ends of the cylinder and forming in cooperation with the cylindrical wall a burette chamber. An inlet is formed in the top cylinder assembly. Means is provided for connecting the other end of the length of flexible tube to the inlet of the top cylinder assembly so that liquid in the tube can be introduced into the burette chamber. The bottom cylinder assembly includes an upwardly extending projection extending into the burette chamber and providing an outlet opening. A filter assembly is carried by the burette and includes a generally conical dome-shaped member forming a generally horizontal recess overlying the upwardly extending projection. The filter assembly includes a hydrophillic filter which provides the only path for the flow of liquid and gas into the recess. The dome-shaped member, the projection and the burette are formed in such a manner so that all liquid entering the burette must pass under the dome-shaped member through the filter and upwardly into the recess and through the outlet whereby any gases collected in the recess are carried out of the burette chamber as liquid passes into the outlet. Tubing is connected to the outlet for withdrawing liquid from the burette chamber and for supplying it to the patient.

In general, it is an object of the present invention to provide an intravenous administration set in which accidental entry of air can be prevented.

Another object of the invention is to provide an administration set of the above character in which air in the solution is filtered out.

Another object of the invention is to provide an administration set in which particulates are filtered out.

Another object of the invention is to provide an administration set in which conventional alarm systems can be utilized.

Another object of the invention is to provide an administration set of the above character which can function as a closed system so that it will remain completely sterile.

Another object of the invention is to provide an administration set of the above character which can be utilized with different types of piercers.

Another object of the invention is to provide an administration set of the above character which can be utilized as a Y-type infusion set.

Another object of the invention is to provide an administration set of the above character which can be utilized as a direct injection set.

Another object of the invention is to provide an administration set of the above character which can be utilized as a burette set.

Another object of the invention is to provide an administration set of the above character which can be utilized as a piggy-back infusion set.

Another object of the invention is to provide an administration set of the above character which can be readily filled.

Another object of the invention is to provide an administration set of the above character which makes it possible to waste very little if any of the liquid being administered.

Another object of the invention is to provide an administration set which utilizes hydrophobic and hydrophillic filters.

Another object of the invention is to provide an administration set of the above character which is attitude independent.

Additional objects and features of the invention will appear from the following description in which the preferred embodiments are set forth in detail in conjunction with accompanying drawings.

BRIEF DESCRIPTION OF THE DRAWINGS

FIG. 1 is a side elevational view of an intravenous administration set incorporating the present invention.

FIG. 2 is an enlarged cross-sectional view of the burette utilized in the administration set shown in FIG. 1.

FIG. 3 is a cross-sectional view taken along the line 3—3 of FIG. 2.

FIG. 4 is a cross-sectional view taken along the line 4—4 of FIG. 2.

FIG. 5 is a cross-sectional view of the vented universal piercer shown in FIG. 1.

FIG. 6 is a cross-sectional view of another burette incorporating the present invention which can be utilized in the administration set.

FIG. 7 is a cross-sectional view taken along the line 7—7 of FIG. 6.

DESCRIPTION OF THE PREFERRED EMBODIMENTS

The intravenous administration set shown in FIGS. 1-5 consists of a length of flexible tube 12 formed of a suitable material such as plastic. Means is provided on one end of the tube 12 in the form of a universal piercer 13 for connecting the flexible tube to a source of intravenous liquid to be supplied to the patient. As shown in FIG. 1, this source of fluid can be any conventional source such as a bottle of intravenous liquid or alternatively a flexible, collapsible bag 14. The construction of the universal piercer will hereinafter be described. The flexible tube 12 has a suitable length as for example 7 inches. A conventional on-off tube clamp 16 is mounted on the flexible tube 12 and provides on-off control of liquid flowing through the flexible tube 12 from the bag 14 and into a burette 17.

The burette 17 is in the form of a calibrated container. In the embodiment shown in FIG. 1, the burette 17 is in the form of a generally cylindrical container and is provided with a cylindrical side wall 21 which has open top and bottom ends. A top cylinder assembly 22 is mounted in the top open end and a bottom cylinder assembly 23 is mounted in the bottom end. The top cylinder assembly 22, the bottom cylinder assembly 23 and the cylindrical side wall 21 in cooperation with each other form a burette or drip chamber 24. The side wall 21 is formed of a suitable material such as plastic. It is preferable for reasons hereinafter described that the side wall be formed of a flexible plastic material and that it be substantially tansparent. The top cylinder assembly 22 is formed of a suitable material such as a rigid plastic and also can be transparent if desired. It is formed with a truncated conical member 26 which extends at a suitable angle as for example 60°. It is also formed by a depending generally cylindrical skirt 27 which is sized so that it fits closely within the upper extremity of the cylindrical side wall 21. The conical member 26 is provided with a lip 28 which seats on the top edge of the cylindrical side wall 21. The central portion of the top cylinder assembly is formed by a generally planar horizontal wall 29 which adjoins the conical member 26. A centrally disposed upwardly extending projection 31 is formed integral with the top wall 29. It is also formed with a downwardly extending projection 32 which extends downwardly into the region circumscribed by the conical member 26. An inlet flow passage 33 extends through the projections 31 and 32. The upper extremity of the upwardly extending projection is relieved by a cut-out 34 so that the other end of the flexible tube 12 can be fitted thereon as shown.

Another upwardly extending projection 36 is formed on the top wall 29 off center from the projection 31 but extends to a substantially lesser height than does the projection 31. It is provided with a tapered vent or opening 37 which extends into an annular recess 38 formed on the lower side of the top wall 29. The annular recess opens into a larger annular recess 39 also formed in the lower side of the top wall 29.

Means is provided for closing the vent or opening 37 and consists of a vent stopper 41. The vent stopper 41 is also formed of a suitable material such as plastic and is formed by a cylindrical member 42 which is slidably mounted upon the portion of the tube 12 which is fitted on the upwardly extending projection 31. The vent stopper 41 is provided with a large cylindrical recess 42 which is of sufficient size so that a substantial clearance space 44 is provided between the inner surface of the cylindrical member 42 and the outer surface of the tube 12. The cylindrical member 42 is provided with a hole 46 which opens into the recess 43. The hole 46 is sized so that there is a fit between the upper extremity of the cylindrical member 42 and the tube 12 so that it can be moved relative to the tube 12 but will be retained in the position to which it is moved by the frictional engagement between the tube 12 and the cylindrical member 42. A pair of bosses 48 are provided on diametrically opposite sides of the cylindrical member 42 and which have provided thereon skirts 49. A tapered depending plug or stopper 51 is carried by each of the bosses 48 and each sized so that it can fit into the tapered vent or opening 37 to close the same merely by pressing the same into the vent or opening 37 with one hand while holding the burette with the other hand. The vent or opening 37 can be opened merely by grasping the skirts 49 and pulling the plug or stopper 51 from the vent or opening 37. To ensure that the vent or opening 37 not will be accidentally closed, the vent stopper 41 can be rotated through 90° so that neither of the plugs 51 can come into engagement with the vent or opening 37. The vent stopper 41 is formed of a plastic material such as polypropylene or polyethylene which is relatively soft and pliable so that it forms an excellent plug or stopper for the vent or opening 31. Qp The vent stopper 41 by being slidably mounted on the tube 12 cannot become accidentally lost or separated from the administration set.

Means is provided for filtering any air which passes into the burette chamber 24 and consists of an annular hydrophobic filter 56. As is well known to those skilled in the art, the hydrophobic filter is a filter which permits the passage of air but which prevents the passage of liquid in either direction. It is formed of a suitable material such as a two micron pore size bacterial filter. The pore size of the material is such that it will only permit bacteria free air to enter into the burette chamber 24. Since the filter is hydrophobic, it will not permit liquid in the chamber to come out of the vent or opening 37 in the event that the burette is tipped upside down after liquid is in the chamber. The hydrophobic filter 56 is held in place by a filter support washer 57. The filter support washer 57 can be secured in place by ultrasonic welding or alternatively by a solvent or cement. Similarly the top cylinder assembly 22 can be secured to the upper extremity of the cylindrical side wall 21 by suitable means such as ultrasonic welding or a plastic cement. p In certain applications in use of the burette 17 it may be desirable to utilize a one-way valve such as the conventional duck-bill valve 61 mounted on the projection 32. The duck-bill valve 61 is formed of a flexible rubber-like material and is formed in such a manner so that liquid can readily pass from the inlet passage 33 through the duck bill valve 61 and into the burette chamber 24. However, as soon as liquid stops passing through the passage 33, duck bill valve 61 will close and will prevent liquid which has passed into the chamber 24 from passing back through the passage 33. The filter support washer 57 is fitted into the annular recess 39. It is provided with a plurality of circumferentially spaced openings 58 which expose the filter 56 and are in registration with the annular recess 38 so that air passing through the vent or opening 37 can pass through the hydrophobic filter 56 and into the burette chamber 24.

The bottom cylinder assembly 23 is also formed of a rigid plastic material of the same type as the top cylinder assembly 22. It is formed by bottom wall 66 which is provided with an inclined surface 67 which slopes outwardly and downwardly from the center. It is also formed by depending skirt 68 which is formed integral therewith. The depending cylindrical skirt 68 is formed so that it forms a tight fit with the lower extremity of the cylindrical wall 21 and is secured thereto by suitable means such as ultrasonic welding or by a cement or solvent. The skirt 68 is provided with a lip 69 which underlies the lower edge of the cylindrical side wall 21.

An upwardly extending centrally disposed projection 71 is formed integral with the wall 66. Similarly, a centrally disposed downwardly extending projection is also formed integral with the wall 66. The two projections 71 and 72 are generally in alignment with each other and are provided with a small bore 73 which is sized so that it is adapted to receive micro-bore tubing 74 which is frictionally retained therein. In addition, a larger bore 76 is provided for receiving a larger size tubing if it is desired to utilize the same. An outlet passage or opening 77 is formed in the upwardly extending projection 71 and opens into the bore 73 and into the flow passage in the tube 74.

A filter dome assembly is disposed within the burette chamber 24 and is mounted upon the upwardly extending projection 71. The filter dome assembly 81 consists of a generally conical dome-shaped member 82 which is formed of a suitable material such as plastic and preferably of a transparent material so that bubble formation can be observed as hereinafter described. The dome-shaped member 82 is positioned so that it forms a generally horizontal recess which has a cone-shaped configuration. The dome-shaped member 82 must be formed of a member which is impervious to liquids or gases. A filter support member 84 is provided as a part of the filter dome assembly 81 and includes an outer rim 86 which is secured to the lower extremity of the dome-shaped member 82 and is bonded thereto by suitable means such as ultrasonic welding or a solvent or cement bond to form an air-tight and liquid-tight bond between the two parts. The filter support member is provided with a central hub 87 and three radially extending spokes 88 which join the rim 86 to the hub 87. A filter member 89 is secured to the lower side of the filter support member 84 in such a manner that an air-tight and liquid-tight connection is formed between the filter member 89 and the filter support member 84. The filter member 89 lies in a horizontal plane as shown. The filter member 89 is formed of a suitable material which will serve as a hydrophillic filter. It is preferably provided with a 0.8 micromillimeter pore size. In connection with the present application for the filter member, a pore size is chosen on the basis of bubble point which will determine the amount of vacuum which can be created behind the wetted filter without introducing air into the system. As hereinafter pointed out, the administration set is to be utilized with an alarm system which will operate in a vacuum between 4 to 10 pounds per square inch. For that reason, a filter has been chosen which has a bubble point which is in excess of 10 psi so it will not interfere with the operation of the alarm system which is utilized with the administration set. It should be appreciated that it is possible to change the sensitivity of the alarm system so that it will operate below 5 psi and when such is the case, it is only necessary that the bubble point be in excess of 5 psi. Thus, the filter material is selected with the pore size so that there is an adequate bubble point to not interfere with the alarm system with a safety factor and still provide a pore size which is as small as possible and practical to permit sufficient flow for filling of the burette. This of course depends on the viscosity of the liquid being introduced through the burette. Thus it is believed that a pore size ranging from 0.6 to 1.2 micromilliliters can be utilized for the filter material and still provide sufficient flow and a high enough bubble point so that it will not interfere with a vacuum type alarm system.

In order to ensure that there is proper spacing between the upper portion of the dome-shaped member 82 and the filter support member 84, spacing means in the form of three legs 91 are formed integral with the dome-shaped member are provided which engage the central hub 87 of the filter support member 84 and are secured thereto by suitable means such as ultrasonic bonding.

The entire filter dome assembly 81 is then mounted upon the upwardly extending projection 71 by seating the hub 87 on the upwardly extending projection 71 and seating it upon an annular raised surface 92 provided integral with the upper wall 66. The filter dome assembly 81 is seated upon the annular surface 92 and is secured thereto, the upper extremity of the upwardly extending projection 71 is in very close proximity to a relatively small circular planar surface 93 which is provided at the upper extremity and centrally disposed on the dome-shaped member 82. This surface 93 is very close to the upper extremity of the projection 71 and in close proximity to the outlet passage 77 so that there is only a very small space 94 provided to allow for air passage during filling and for liquid after completion of fill.

The burette 17 is provided with an injection site 101 in the lower extremity of the same. This injection site is formed by a cylindrical extension 102 which is formed as a part of the bottom cylinder assembly and is formed integral with the bottom wall 66 and extends downwardly therefrom. A small upwardly extending projection 103 which is disposed off-center extends upwardly into the burette chamber and is positioned so that it clears vertically and laterally the filter dome assembly 81 as shown in FIG. 2. An outlet passage 104 extends through the projection 103 and through the cylindrical extension 102. The cylindrical extension 102 is also provided with a bore 106 which is adapted to receive a Lure tapered needle adapter if so desired which opens into the passage 104. A cap 107 is provided on the cylindrical extension 102 for closing the cylindrical extension and is of a type which can be penetrated by a needle through a rubber plug 108 so that drugs can be injected into the injection site. Alternatively by removing the cap 107, the injection site can be utilized as a means for emptying the burette as hereinafter described.

The remainder of the administration set is substantially conventional. As shown in FIG. 1, the tube 74 which is connected to the burette is connected into the inlet of a conventional pump 111 which is of the type described in copending application Ser. No. 689,115 filed on May 24, 1976. As disclosed in said copending application, the pump is adapted to be driven by a pump actuator to cause fluid to be pumped from the burette 17 and to be supplied to an outlet tube 112. A roller clamp 115 is mounted on the outlet tube 112 and is provided for flow regulation and on-off control of fluid through the tube 112. An injection site 113 is provided at the end of the tube 112. The injection site is provided with a cap 114 which can be penetrated with a needle to introduce drugs and the like. The injection site 113 is connected to another tube 116. The tube 116 has a needle adapter 117 carried thereby. The needle adapter 117 is adapted to receive a needle which is adapted to be introduced into the veins of a patient to permit the administration of an intravenous fluid to the patient utilizing the administration set.

The construction of the universal piercer is shown in FIG. 5. The universal piercer consists of a spike 121 which is the type described in U.S. Pat. No. 4,055,176. In said U.S. Pat. No. 4,055,176, the spike is associated with a drip chamber. In the present application of the spike, the drip chamber has been eliminated because its function is served by the burette and a tube connector 122 has been substituted in its place. The tube connector 122 is formed of a suitable material such as plastic. It is provided with a generally tapered cylindrical extension 123 having an annular recess 124 at its lower extremity to receive the tube 12 to be connected thereto. The tube connector 122 is provided with a skirt 126 which is adapted to fit into the lower extremity of the spike 121 and to be secured thereby by suitable means such as ultrasonic welding. A hydrophobic filter member 127 is disposed in the spike 121 as disclosed in said U.S. Pat. No. 4,055,176 to prevent the introduction of bacteria into an unvented bottle during the time that the spike is being inserted into the bottle. A small opening 128 is provided between the skirt 126 and the spike to permit the introduction of air through the filter 127 and into the spike. This assembly can be identified as a universal piercer 13 as hereinbefore described which makes it possible to be utilized with different types of bottles, bags and the like containing the liquids to be intravenously introduced. Thus it can be utilized with containers which must be vented as well as those which do not require venting.

By way of example, an administration set incorporating the present invention was provided with a tube 12 having a length of approximately 7 inches and having an i.d. of 0.090 inches and an o.d. of 0.140 inches. The burette was approximately 1¾ inches in diameter and had a sufficient length so that the drip chamber or burette chamber 24 contained at least 50 milliliters. Such a 50 milliliter scale (not shown) was provided on the burette so that the extent of filling could be ascertained. The tubing 74, 112 and 116 utilized was microtubing and had an internal diameter of 0.050 inches and an outside diameter of 0.090 inches.

Operation and use of the administration set may now be briefly described as follows. To fill the administration set, the universal piercer 13 is inserted into the container 14 with the roller clamp 113 distal of the pump set 111 closed and with the vent stopper 41 in a position so that one of its plugs or stoppers 51 is closing the vent or opening 37. The container is then hung and the on-off clamp 16 is opened. The administration set can now be filled by sequeezing the flexible cylindrical wall 21 forming the burette or drip chamber 24 until sufficient liquid has been drained from the container 14 and passes through tube 7 into the inlet flow passage 33 through the duck bill valve 61 and into the chamber 24 until the chamber 24 is filled to a suitable depth as for example approximately 10 to 12 milliliters of fluid in a graduated burette which has been graduated for 50 milliliters.

As the liquid enters the chamber 24, it will first come in contact with the inclined surface 67 and will cause any air trapped ahead of the liquid to be moved upwardly and into contact with the hydrophillic filter 89 and to be urged through the filter. This will occur until the filter is wetted. As the level of liquid in the chamber 24 rises, the liquid will wet the filter 89. As soon as the filter 89 is wet because of its inherent characteristics, it will prevent the passage of further air therethrough up to the bubble point pressure. As the level of the liquid in the chamber 24 increases, additional liquids will pass through the filter 89 and will gradually fill the recess 83 and push ahead of it any air which is passed through the filter and which is in the recess 83. This air will be pushed to the top and into the space 94. As the liquid rises to the level of the space 94, the liquid will travel into the outlet passage 77 and carry with it any air when has been entrapped within the recess 83. In the event that any air bubbles remain in the space 94, the burette can be lightly tapped to cause the air bubbles to travel outwardly through the outlet passage 77 with the liquid. The transparency of the filter dome member 82 and the side wall 21 facilitates the ascertainment of the presence of bubbles within the recess 83. Thus it can be seen that as soon as all the air has been eliminated from the recess 83, no further air can be introduced therein after the filter 89 has been wetted because of the characteristics of the filter which prevent any further introduction of air unless the bubble point pressure is exceeded.

As pointed out previously, the filter material is chosen so that it has a bubble point pressure which is substantially above the vacuum condition which is required for generating of an alarm in the event of the burette being emptied of liquid during intravenous administration. The seven inch length of tube 12 provides a sufficient head to cause filling of the burette chamber 24 to the height hereinbefore described and to cause wetting of the hydrophillic filter 89. This head also aids in filling the microtubing 74, 112 and 116. This is accomplished by opening the on-off roller clamp 113 and holding the pump in a position so that its outlet end is facing upwardly so that any air passing out from under the filter dome assembly passes through the microtubing through the pump cassette 11, the microtubing 112, through the injection site 113, through the microtubing 116 and through the needle adapter 117. As soon as all the air has been removed from the tubing, the needle can be placed on the needle adapter and the needle inserted into the veins of the patient in a conventional manner. The pump set 111 can then be placed in a pump actuator and can be operated in the manner described in copending application Ser. No. 689,115 filed May 24, 1976. When the burette chamber or drip chamber 24 is filled in this manner, the chamber 24 will act as a drip chamber and liquid as introduced into the drip chamber will appear as drops from the one-way duck bill valve 61 to maintain the 10 to 12 cc level which has previously been established in the drip chamber.

Regardless of the attitude of the burette, no air will be introduced into the system because the hydrophillic filter will prevent air from entering into the recess 83. Thus, the burette is in fact attitude independent and can operate satisfactorily without any danger of introducing air into the microtubing and into the patient.

In the event that the supply of liquid in the container 14 is exhausted, the liquid level in the burette chamber 24 will continue to lower until all that remains below the hydrophillic filter 89 is air. As the pump cassette 111 attempts to suck additional liquid from the burette chamber 24, a vacuum condition will be created which will be sensed by the alarm system described in U.S. Pat. No. 4,056,333. This will cause an alarm to be actuated so that the nurse can be alerted that more liquid is required for the patient.

If it is now desired to convert the administration set to a burette set, the on-off clamp 16 must be closed and the vent stopper 41 removed to open the vent 36. This is accomplished by pulling the vent stopper upwardly and rotating it approximately 90° to an out-of-the-way position. When this is the case, the pump cassette 111 will only draw liquid from the burette chamber 24 and when it is emptied, an alarm will be sounded in the manner hereinbefore described.

The administration set can be utilized as a Y-set. An additive set of any type can be utilized and can be filled with the desired drug and its needle associated therewith can be inserted into the injection site 101 provided on the burette. It should be appreciated that if desired the cap 107 can be removed and a conventional "Luer" connection needle adapter can be directly mounted on the injection site without the use of a needle. During this operation, the on-off tube clamp 16 must be closed. The on-off vent stopper 41 can either be left open or closed as desired. If it is left open, the additive drug will fill the entire burette chamber 24. Spill over is prevented from the burette chamber 24 because the hydrophobic vent filter will prevent liquid from passing out of the chamber 24. Such a method of providing an additive to the patient is very advantageous. The dilution factor is minimal since only 10 to 12 cc of base fluid is diluted with 50 cc of additive drug fluid. The base fluid remaining in the microtubing and the cassette distal to the hydrophillic filter 89 proximal to the patient is only 5 milliliters which is a very minimal amount of dilution. The patient will thus receive his additive drug without any significant delay. If it is desired to reduce the dilution even further, it is possible (when no one-way valve 61 is utilized) to return all the base solution in the chamber 24 to the bottle or bag by inverting the burette and lowering the bottle. In such a procedure the on-off vent stopper 41 must be in the open position and the on-off tube clamp 16 must be opened. If the vent stopper is closed, the liquid level in the chamber 24 will remain constant and the dilution factor will be reduced more gradually. By opening the vent stopper and lowering the drug additive bottle, the drug additive drug in the burette chamber 24 can be returned to the bottle. The sterilized integrity of the set will remain intact due to the hydrophobic bacterial air filter incorporated in the top cylinder assembly 22.

Injections of drugs can be made directly into the burette chamber 24 utilizing the injection site 101 without fear of introducing particulate matter and without concern for introducing air into the administration set. There is therefore no need for prefiltering.

The use of the one-way valve 61 makes possible drug infusion by means of the injection site and utilizing another container. By way of example, the bag or the container carrying the drug can be suspended so that it is higher than the liquid contained in the bag 14. When this is the case, the liquid will preferentially be taken from the drug bag and as soon as the drug bag is empty, the liquid from the other container 14 will be introduced by the pump 111. Thus it can be seen there will be an automatic cut-over from the drug solution to the other solution as for example a base solution carried by the container 14. The one-way valve 61 also prevents the drug solution from entering into the container carrying the other solution as for example a base solution.

It should be appreciated that if desired the administration set can be utilized without a one-way valve 61. When the one-way valve 61 is utilized, liquid within the chamber 24 can be drained out of the chamber 24 by removing the cap 107 from the injection site.

Another embodiment of the invention is shown in FIGS. 6 and 7 in which a burette 131 of a different type is provided. The upper extremity of the burette 131 can be identical to the burette 17 however with the exception that it would have a rectangular configuration rather than a circular or cylindrical configuration. The burette 131 is provided with vertical side walls 132 which form a drip chamber 133. A bottom assembly 136 is mounted in the lower extremity of the drip chamber 123 and consists of a member 137 which is generally U-shaped in cross-section and which has its upper extremity fitted into the lower extremity of the burette chamber 133. A cover 138 is mounted in the member 137 and is bonded thereto to form an air-tight and liquid-tight space within the member 137 and the cover 138.

A filter support member 139 is mounted in the U-shaped member 137 and carries a hydrophillic filter 141 of the type hereinbefore described. A space 143 is provided between the cover 143 and the filter support member 139 and is in communication with an outlet flow passage 144 that opens into the lower extremity of the drip chamber 133. A space 146 is provided on the other side of the filter support member 139 and extends upwardly into a narrow slot or recess 147 at the upper extremity of the rear wall 148 of the U-shaped member 137. As can be seen in FIG. 6, the wall 148 terminates in a position to provide the relatively small slot or recess 147 to receive air. This slot or recess 147 is in communication with a flow passage 149 which extends downwardly and is formed in a longitudinally extending protrusion provided on the rear of the U-shaped member 137 shown in FIG. 7. A protrusion 151 is formed integral with the U-shaped member and is provided with a bore 152 for receiving one end of microtubing 153. The tubing 153 is connected to the pump cassette 111 in the same manner as the microtubing 74.

Operation of this embodiment of the burette is very similar to that hereinbefore described. As liquid enters into the drip chamber 133, it will flow downwardly through the flow passage 144 into the space 143 to the bottom of the space. As additional liquid flows into the space 143, the liquid level will rise and will progressively wet the hydrophillic filter 141 and cause any air therein to be introduced through the filter into the space 146. At the same time the level of the liquid in the space 146 will be rising to cause the air to be raised upwardly into the slot 147. As the liquid rises to the level of the slot 147 and begins to flow into the outlet passage 149, it will carry with it any air which has been forced into the slot and carry it out through the microtubing 153 into the atmosphere in the manner hereinbefore described in connection with filling of the first embodiment of the administration set. Thus it can be seen that the same principles are utilized in this embodiment of the burette in that any air which is on one side of the hydrophillic filter is removed from the burette and thereafter since the hydrophillic filter has been wetted, further air is prevented from passing onto the other side of the filter thus making the burette attitude independent. In other words, no matter what the position of the burette, there is no danger of introducing air into the patient after the administration set has been properly filled.

From the foregoing it can be seen that there has been provided an administration set which is of a universal type and which can be utilized without any danger of injecting air into the patient. It is attitude independent. It can be utilized as a Y-infusion set, a drug injection set, a burette set and piggy-back infusion set. Patient safety will not be comprised because particulates created by injectibles, drug additives piercing the I.V. bottle, in manufactured solutions and the like will be removed by the hydrophillic filter. Any air in the solution will be filtered by the filter assembly which acts as a gas filter. Once the administration set has been properly filled, it is physically impossible to introduce air into the filter assembly. Accidental entry of air by bottle inversion, by the spike coming out of the bottle or by injections through the proximal injection site located in the burette are prevented. In the event air accumulates on the distal side of the filter assembly, an alarm will be sounded. The set is provided with a hydrophobic vent and thus assures maintaining sterility of the set. Since very small amounts of liquid are utilized in the set, the set can be readily used with infants.

What is claimed is:

1. In an administration set for use with a source of liquid to be administered intravenously, a length of flexible tubing, means carried by one end of the tube adapted to be connected to the source of fluid, means forming a vertically disposed container having a drip chamber therein, means connecting the other end of the flexible tubing to the chamber so that liquid flowing through the flexible tubing will flow into the chamber, a filter assembly carried by the container and having a dome shaped member having inclined wall portions impervious to liquid and defining a dome-shaped recess having a larger open end which is oriented to face downwardly, projecting means extending into the dome-shaped recess in the filter assembly and having an outlet flow passage in communication with the dome-shaped recess in the filter assembly, the filter assembly having an inlet opening into the dome-shaped recess and including a hydrophilic filter covering the inlet and providing the only flow passage means so that any air and liquid passing into the dome-shaped recess must pass through the hydrophilic filter and means in communication with the outlet passage adapted to be coupled to the patient, the filter assembly being formed so that as liquid is introduced into the chamber, the hydrophilic filter will be progressively wetted to cause liquid to be introduced into the dome-shaped recess in the filter assembly and to cause substantially all of the air in the dome-shaped recess to be carried out of the dome-shaped recess by the passage of liquid from the dome-shaped recess into the outlet passage.

2. In an administration set for use with a source of liquid to be administered intravenously, a length of flexible tubing, means carried by one end of the tube adapted to be connected to the source of fluid, means forming a container having a drip chamber therein, means connecting the other end of the flexible tubing to the chamber so that liquid flowing through the flexible tubing will flow into the chamber, a filter assembly carried by the container and having a recess formed therein, projecting means extending into the filter assembly and having an outlet flow passage in communication with the recess in the filter assembly, the filter assembly having an inlet opening into the recess and including a hydrophilic filter covering the inlet and providing the only flow passage means so that any air and liquid passing into the recess must pass through the hydrophilic filter and means in communication with the outlet passage adapted to be coupled to the patient, the filter assembly being formed so that as liquid is introduced into the chamber, the hydrophilic filter will be progressively wetted to cause liquid to be introduced into the recess in the filter assembly and to cause substantially all of the air in the recess to be carried out of the recess by the passage of liquid from the recess into the outlet passage, said filter assembly being formed in such a manner that there is only a relatively small space between the projection means extending into the filter assembly and the upper extremity of the filter assembly so that air which collects in the space will be carried through the outlet passage.

3. In an administration set for use with a source of liquid to be administered intravenously, a length of flexible tubing, means carried by one end of the tube adapted to be connected to the source of fluid, means forming a container having a drip chamber therein, means connecting the other end of the flexible tubing to the chamber so that liquid flowing through the flexible tubing will flow into the chamber, a filter assembly carried by the container and having a recess formed therein, projecting means extending into the filter assembly and having an outlet flow passage in communication with the recess in the filter assembly, the filter assembly having an inlet opening into the recess and including a hydrophilic filter covering the inlet and providing the only flow passage means so that any air and liquid passing into the recess must pass through the hydrophilic filter and means in communication with the outlet passage adapted to be coupled to the patient, the filter assembly being formed so that as liquid is introduced into the chamber, the hydrophilic filter will be progressively wetted to cause liquid to be introduced into the recess in the filter assembly and to cause substantially all of the air in the recess to be carried out of the recess by the passage of liquid from the recess into the outlet passage, said filter assembly including a filter member having a generally dome-shaped configuration and wherein said recess is generally dome-shaped as defined by said dome-shaped member.

4. In an administration set for use with a source of liquid to be administered intravenously, a length of flexible tubing, means carried by one end of the tube adapted to be connected to the source of fluid, means forming a container having a drip chamber therein, means connecting the other end of the flexible tubing to the chamber so that liquid flowing through the flexible tubing will flow into the chamber, a filter assembly carried by the container and having a recess formed therein projecting means extending into the filter assembly and having an outlet flow passage in communication with the recess in the filter assembly, the filter assembly having an inlet opening into the recess and including a hydrophilic filter covering the inlet and providing the only flow passage means so that any air and liquid passing into the recess must pass through the hydrophilic filter and means in communication with the outlet passage adapted to be coupled to the patient, the filter assembly being formed so that as liquid is introduced into the chamber, the hydrophilic filter will be progressively wetted to cause liquid to be introduced into the recess in the filter assembly and to cause substantially all of the air in the recess to be carried out of the recess by the passage of liquid from the recess into the outlet passage, said container includes means for forming a vent which is open to the atmosphere, a hydrophilic filter carried by the container so that any air passing through the vent must pass through the hydrophobic filter and means carried by the container for selectively closing and opening said vent.

5. A set as in claim 4 wherein said means for selectively closing and opening said vent includes a vent stopper slidably mounted on said flexible tubing and having at least one plug carried thereby adapted to be inserted into said vent.

6. In an administration set for use with a source of liquid to be administered intravenously, a length of flexible tubing, means carried by one end of the tube adapted to be connected to the source of fluid, means forming a container having a drip chamber therein, means connecting the other end of the flexible tubing to the chamber so that liquid flowing through the flexible tubing will flow into the chamber, an injection site carried by said container at the lower extremity thereof, a filter assembly carried by the container and having a recess formed therein, projecting means extending into the filter assembly and having an outlet flow passage in communication with the recess in the filter assembly, the filter assembly having an inlet opening into the recess and including a hydrophilic filter covering the inlet and providing the only flow passage means so that any air and liquid passing into the recess must pass through the hydrophilic filter and means in communication with the outlet passage adapted to be coupled to the patient, the filter assembly being formed so that as liquid is introduced into the chamber, the hydrophilic filter will be progressively wetted to cause liquid to be introduced into the recess in the filter assembly and to cause substantially all of the air in the recess to be carried out of the recess by the passage of liquid from the recess into the outlet passage.

7. In an administration set for use with a source of liquid to be administered intravenously, a length of flexible tubing, means carried by one end of the tube adapted to be connected to the source of fluid, means forming a container having a drip chamber therein, means connecting the other end of the flexible tubing to the chamber so that liquid flowing through the flexible tubing will flow into the chamber, a filter assembly carried by the container and having a recess formed therein, projecting means extending into the filter assembly and having an outlet flow passage in communication with the recess in the filter assembly, the filter assembly having an inlet opening into the recess and including a hydrophilic filter covering the inlet and providing the only flow passage means so that any air and liquid passing into the recess must pass through the hydrophilic filter and means in communication with the outlet passage adapted to be coupled to the patient, the filter assembly being formed so that as liquid is introduced into the chamber, the hydrophilic filter will be progressively wetted to cause liquid to be introduced into the recess in the filter assembly and to cause substantially all of the air in the recess to be carried out of the recess by the passage of liquid from the recess into the outlet passage said container being substantially cylindrical and being provided with a synlidrical side wall having open ends, a top cylinder assembly mounted in one end of the said cylindrical wall and a bottom cylinder assembly mounted in the other end of the cylindrical wall, the bottom cylinder assembly including a bottom wall, a centrally disposed projection extending through the bottom wall and having an outlet flow passage therein, said cylindrical wall and said top cylinder assembly and said bottom cylinder assembly defining said drip chamber, said filter assembly being mounted in said drip chamber.

8. In an administration set for use with a source of liquid to be administered intravenously, a length of flexible tubing, means carried by one end of the tube adapted to be connected to the source of fluid, means forming a container having a drip chamber therein, means connecting the other end of the flexible tubing to the chamber so that liquid flowing through the flexible tubing will flow into the chamber, a filter assembly carried by the container and having a recess formed therein, projecting means extending into the filter assembly and having an outlet flow passage in communication with the recess in the filter assembly, the filter assembly having an inlet opening into the recess and including a hydrophilic filter covering the inlet and providing the only flow passage means so that any air and liquid passing into the recess must pass through the hydrophilic filter and means in communication with the outlet passage adapted to be coupled to the patient, the filter assembly being formed so that as liquid is introduced into the chamber, the hydrophilic filter will be progressively wetted to cause liquid to be introduced into the recess in the filter assembly and to cause substantially all of the air in the recess to be carried out of the recess by the passage of liquid from the recess into the outlet passage, said hydrophilic filter having a bubble point in excess of 5 psi.

9. A set as in claim 8 wherein said hydrophilic filter has a pore size ranging from 0.5 to 1.2 micromillimeters.

10. A set as in claim 4 wherein said hydrophobic filter has a pore size of approximately 0.2 micromillimeters so as to serve as a bacterial filter.

11. In an administration set for use with a source of liquid to be administered intravenously, a length of flexible tubing, means carried by one end of the tube adapted to be connected to the source of fluid, means forming a container having a drip chamber therein, means connecting the other end of the flexible tubing to the chamber so that liquid flowing through the flexible tubing will flow into the chamber, a filter assembly carried by the container and having a recess formed therein, projecting means extending into the filter assembly and having an outlet flow passage in communication with the recess in the filter assembly, the filter assembly having an inlet opening into the recess and including a hydrophilic filter covering the inlet and providing the only flow passage means so that any air and liquid passing into the recess must pass through the hydrophilic filter and means in communication with the outlet passage adapted to be coupled to the patient, the filter assembly being formed so that as liquid is introduced into the chamber, the hydrophilic filter will be progressively wetted to cause liquid to be introduced into the recess in the filter assembly and to cause substantially all of the air in the recess to be carried out of the recess by the passage of liquid from the recess into the outlet passage, and a oneway valve coupled to the inlet flow passage so that liquid introduced into the chamber must pass through the one-way valve.

12. In an administration set for use with a source of liquid to be administered intravenously, a length of flexible tubing, means carried by one end of the flexible tubing adapted to be connected to the source of fluid, said container comprising a generally cylindrical flexible wall having open top and bottom ends, a top cylinder assembly disposed in the top end of the cylinder, a bottom cylinder assembly disposed in the bottom end of the cylindrical wall, said cylindrical wall and said top cylinder assembly and said bottom cylinder assembly in cooperation with each other forming a drip chamber, inlet flow passage means provided in the top cylinder assembly in communication with the drip chamber, means connecting the other end of the flexible tubing to the inlet flow passage means, said bottom cylinder assembly including a bottom wall, a projection extending upwardly through the bottom wall and into the drip chamber and having an outlet flow passage therein, means connected to the outlet flow passage adapted to be placed in communication with the veins of the patient, a filter assembly mounted within the drip chamber upon the projection, said filter assembly having a recess formed therein, said projection extending into said recess, said filter assembly also including a hydrophilic filter enclosing at least one side of said recess so that the only entrance for air and liquid into the recess is through the hydrophilic filter said filter assembly being formed so that the hydrophilic filter is wetted by liquid introduced into the chamber prior to the filling of the recess so that the hydrophilic filter is wetted as the recess is being filled whereby air within the recess is carried out through the outlet passage as liquid flows through the outlet passage so that substantially no air remains in the recess said top cylinder assembly including a vent which is open to the atmosphere, a hydrophobic filter carried by the top cylinder assembly and being disposed so the air entering through the vent must pass through the filter assembly into the drip chamber and means for closing said vent.

13. A set as in claim 12 wherein said bottom wall is inclined upwardly and inwardly and wherein said hydrophilic filter lies in a generally horizontal plane with respect to said inclined bottom wall.

14. A set as in claim 12 wherein said filter assembly includes a dome-shaped member overlying the hydrophilic filter and wherein the central portion of the dome-shaped member is disposed in the vicinity of the entrance of the outlet passage.

15. An administration set as in claim 14 wherein a small space is provided between the dome-shaped member and the upper extremity of the projection.

16. A set as in claim 12 together with an injection site extending through the bottom wall and being disposed off to the side of the filter assembly.

17. A set as in claim 12 wherein said means for closing said vent includes a vent stopper slidably mounted on said tube and a plug carried by said stopper adapted to be inserted into said vent.

18. A set as in claim 12 together with a one-way valve disposed within the chamber and connected to the inlet passage so that liquid flowing into the chamber must flow through the one-way valve.

19. In a container for use with an administration set of the type used with a source of liquid to be administered intravenously, means forming a chamber and including an inlet flow passage in communication with the chamber and an outlet flow passage in communication with the chamber and a filter assembly disposed within the chamber, said filter assembly having a recess formed therein and having a hydrophilic filter enclosing at least one side of the recess and serving as the only means for permitting air and liquid to enter into the recess, said filter assembly being mounted so that said outlet passage is solely in communication with said recess at the upper extremity of the recess, said filter assembly being formed so that as liquid is introduced into the chamber, the hydrophilic filter is wetted and substantially all air in the recess is carried outwardly through the flow passage as the recess is filled with liquid.

20. A container as in claim 19 wherein said outlet passage is formed by a projection extending into the recess and wherein said filter assembly is provided with a member impervious to air and liquid which is in close proximity to said projection so that only a relatively small space is provided between the projection and the member whereby air within the recess is readily carried from the recess through the outlet passage.

* * * * *